United States Patent [19]

Ronc

[11] 4,109,354
[45] Aug. 29, 1978

[54] MANUFACTURE OF TAMPONS

[75] Inventor: Marcel Ronc, Zurich, Switzerland

[73] Assignee: Karl Ruggli AG, Fisibach, Switzerland

[21] Appl. No.: 691,013

[22] Filed: May 28, 1976

[30] Foreign Application Priority Data

May 30, 1975 [CH] Switzerland .................. 6973/75

[51] Int. Cl.² ........................................ D04H 1/22
[52] U.S. Cl. ................................................. 28/119
[58] Field of Search ............... 19/144.5, 149; 128/270, 128/285; 100/232; 28/118, 119

[56] References Cited

U.S. PATENT DOCUMENTS

| | | | |
|---|---|---|---|
| 2,263,909 | 11/1941 | Webb | 19/144.5 |
| 2,798,260 | 7/1957 | Neipmann et al. | 19/144.5 |
| 3,422,496 | 1/1969 | Wolff et al. | 19/144.5 |

*Primary Examiner*—Dorsey Newton
*Attorney, Agent, or Firm*—William J. Daniel

[57] ABSTRACT

This invention relates to machines for the manufacture of tampons, the machines having a first set of $n$ pressing dies arranged around a common central axis for pivotal movement together from a separated position for receiving a tampon blank inwardly toward a common axis to a compression position compressing the blank into a shaped tampon and then back to the separated position. Each such first die has generally converging arcuately curved concave and convex surfaces which define therebetween an included angle equal to about $360/n$ with these curvatures generally mating respectively with the respectively adjacent convex and concave surfaces of other dies on either side to define a narrow arcuately curved gap or slot between the mutually mating surfaces of each adjacent pair of first dies. A cooperating second set of $n$ dies is also arranged for pivotal movement around the common central axis, each second die being disposed for movement toward and from similar separated and compression positions within the arcuately curved gaps or slots between adjacent pairs of first dies after the latter are in their compression position and having opposed concave and convex surfaces mating with the curvatures of the mutually facing surfaces of each pair of first dies which define such gap. Each second die can share a common pivot axis with an adjacent first die.

11 Claims, 8 Drawing Figures

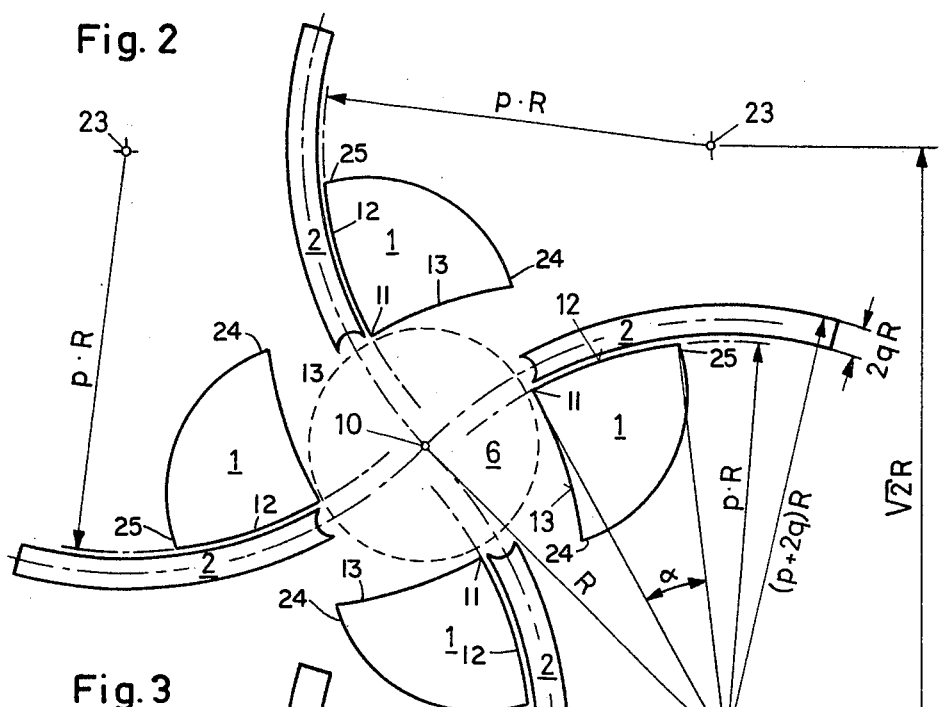
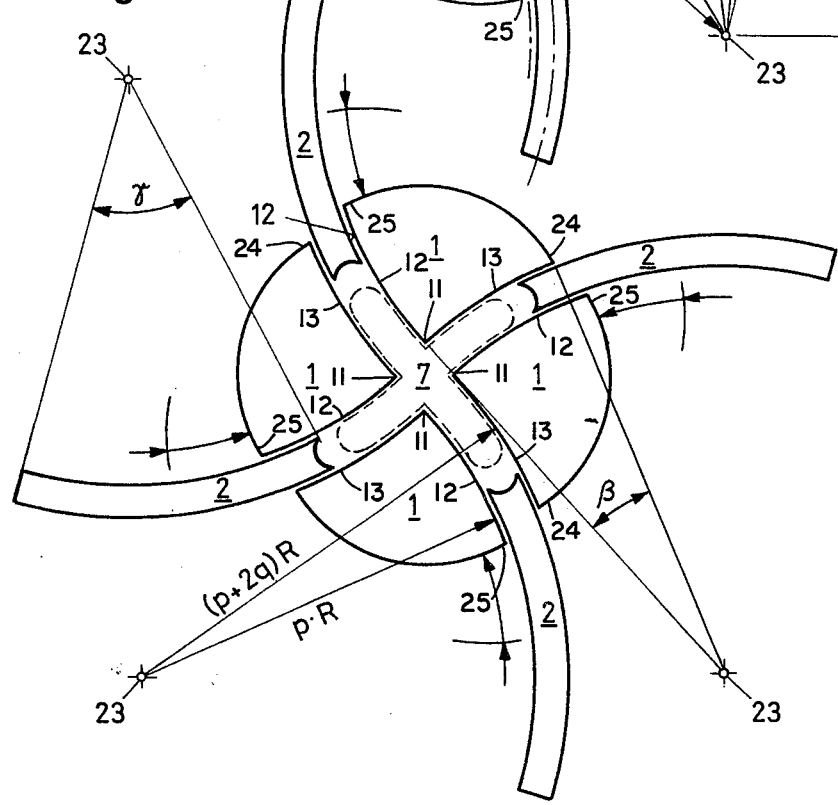

MANUFACTURE OF TAMPONS

This invention relates to a machine for manufacture of tampons, particularly for feminine hygiene.

Machines for the manufacture of tampons have been known for a long time, for example from U.S. Pat. No. 2,798,260. This known machine has the disadvantage that the tampons produced thereby have inadequate resistance to buckling, and therefore on insertion or attempted insertion into hollow carrier tubes they buckle. It therefore became necessary to develop procedures, such as are described, for example, in German OLS No. 1,491,161, for operating this known machine to reduce this tendency of the tampons to buckle.

According to the present invention there is provided a machine for manufacturing a tampon, particularly for feminine hygiene, by pressing a substantially elongated cylindrical blank of wound wadding fleece in directions generally radially of the blank axis, the machine comprising a first set of pressing dies, $n$ number, disposed around a central axis and movable towards said central axis to a compression postion, each die having two pressing surfaces converging at an included angle of $360°/n$ towards a pressing edge extending parallel to said central axis the mutually facing pressing surfaces of each adjacent pair of dies defining therebetween a gap-like path or slot when in their compression position; a second set of pressing dies, also $n$ in number, alternating with the dies of the first set around the central axis and likewise pivotally movable towards such axis, each second die being movable within one of said gap-like paths and having a concave pressing surface at its inner edge or face forming a groove-like depression extending parallel to said central axis; first and second drive means for respectively moving the first or second sets of pressing dies towards said central axis and first and second coupling means for coupling the respective first or second pressing dies together so that corresponding points on the respective sets remain at equal distances from said central axis. The dies of each set are mounted for pivotal movement towards the central axis about pivot axes parallel to the central axis, and adjacent dies from each set can share a common pivot axis. The pivot axes are spaced a distance R from the central axis and a distance $2 R \sin \pi/n$ from one another, R being greater than D/2 and at least $$\frac{D}{4} \{k + (1 + \sin \frac{\pi}{n}) \}c^2/k.$$

Each die of the first set has two generally converging arcuate pressing surfaces one of which is concave and the other convex. The convex surface has a radius of curvature about its own pivot axis of at least approximately $p \cdot R$ and a dimension extending generally radially of the center axis which can be expressed in terms of angle $\alpha$ of at least $$\alpha_{min} = \text{arc cos} \{ \frac{1}{2} (p + \frac{1}{p}) - \frac{d}{p} \} - \text{arc sin } q.$$

The concave surface of each die 1 has a radius of curvature about the pivot axis of the corresponding second die of at least approximately $\{p + 2 q \, tg \, \pi/n\}R$. Each die of the second set is an arcuate sector of an annulus having a wall thickness of at least approximately $2 q \, tg \, \pi/n \cdot R$, which has a concave surface with a radius of curvature of at least approximately $p \cdot R$, and a convex surface having a radius of curvature of at least approximately $\{p + 2q \, tg \, \pi/n\} R$ both with respect to the pivot axis of that die. The inward end of the annular sector of each second die has a concave surface facing the central axis and forming a groove-like pressing surface having a groove depth of at least approximately $(b - q) R$, wherein $p = \sqrt{1 - q^2} - q \, tg \, \pi/n$ and $q = a \cos \pi/n$, in which $a = r_i/R$, $b = r_a/R$, $c = 2r_i/D$, $d = D^2/8 \cdot R^2$ and $$k = \frac{1 - c \cdot \sin \frac{\pi}{n}}{1 - \sin \frac{\pi}{n}},$$

D being the diameter of the blank, and $r_1$ is the smallest and $r_a$ the greatest distance between the center and external surface of the fully compressed tampon.

The invention further provides a method of manufacture of a tampon using a machine according to the invention, which comprises bringing first and second sets of dies into angular positions about a central axis which are displaced relative to angular positions during compression by a pivot angle equal to at least $\alpha_{min}$, the pivot angle for the second dies being smaller than the sector angle of the concavely curved pressing surfaces of the first die, introducing a blank into the space between the sets of pressing dies, moving the first dies toward the central axis until they engage the second dies, and moving the second dies to compression position to compress the blank into a tampon.

A machine embodying the invention will now be described, by way of example, with reference to the accompanying diagrammatic drawings in which:

FIGS. 2 to 5 show individual operating stages of the machine of FIG. 1;

Figure 1:
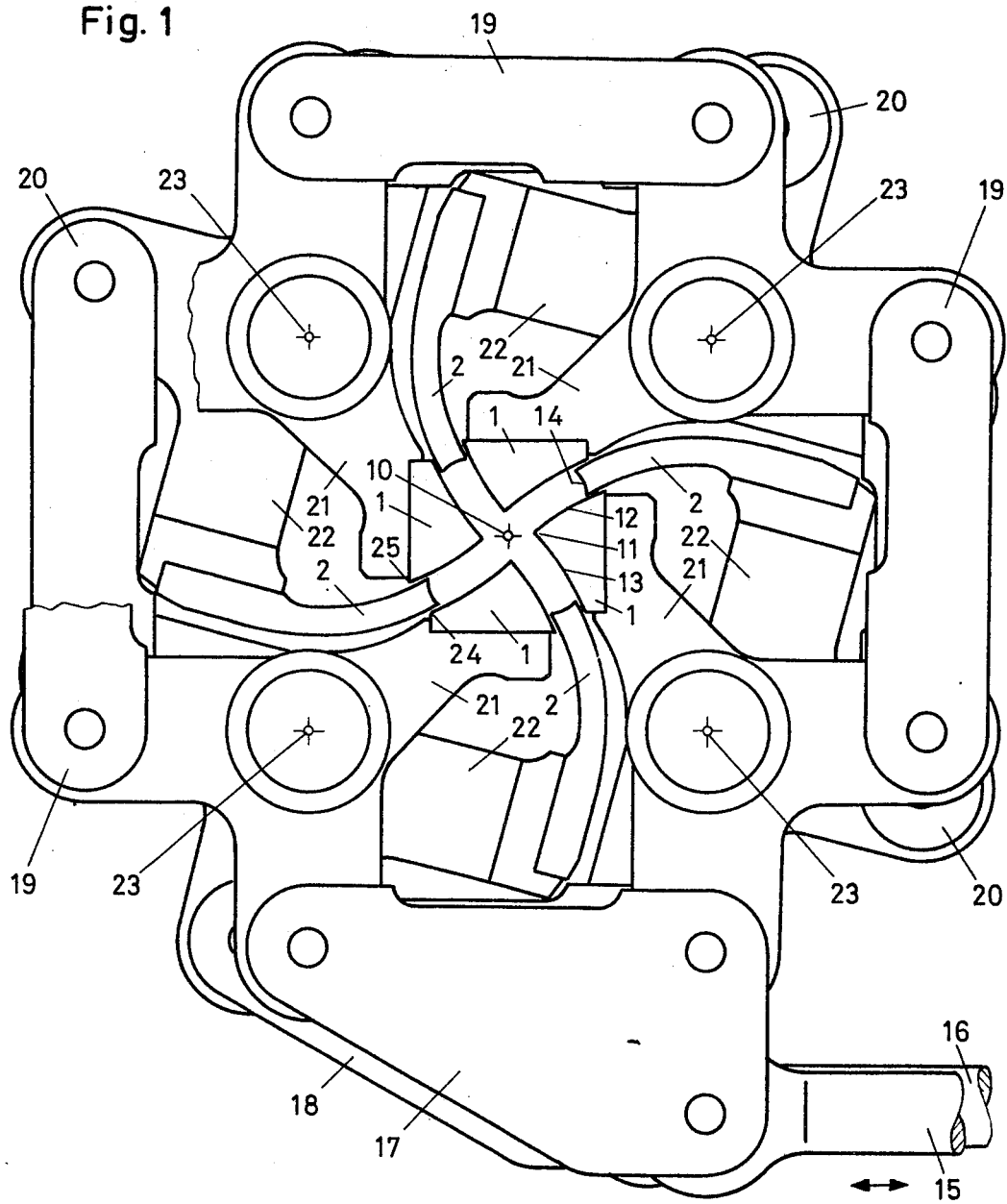
FIG. 1 is a plan view of the machine.
Figure 6:
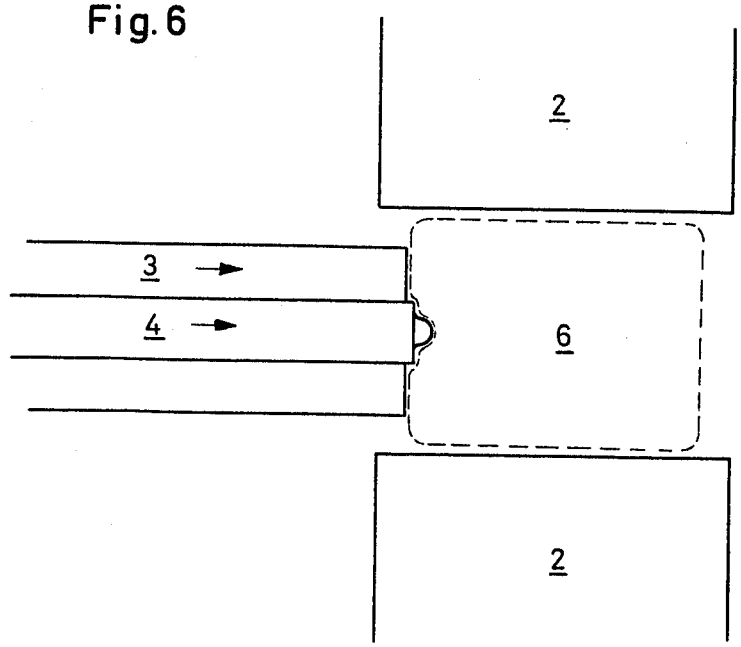
Figure 7:
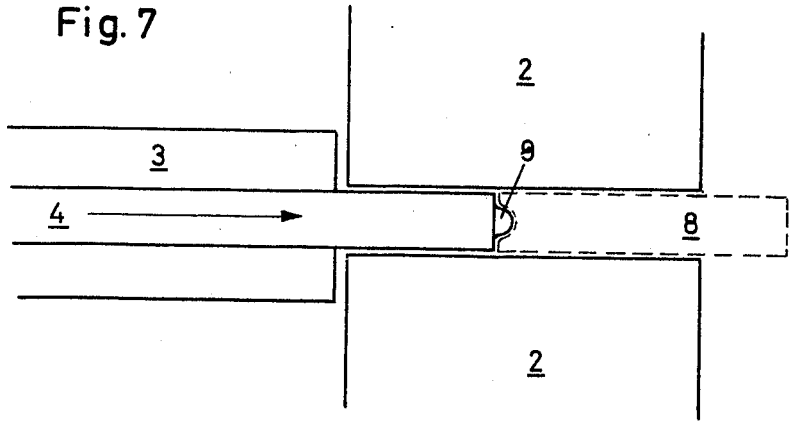
Figure 8:
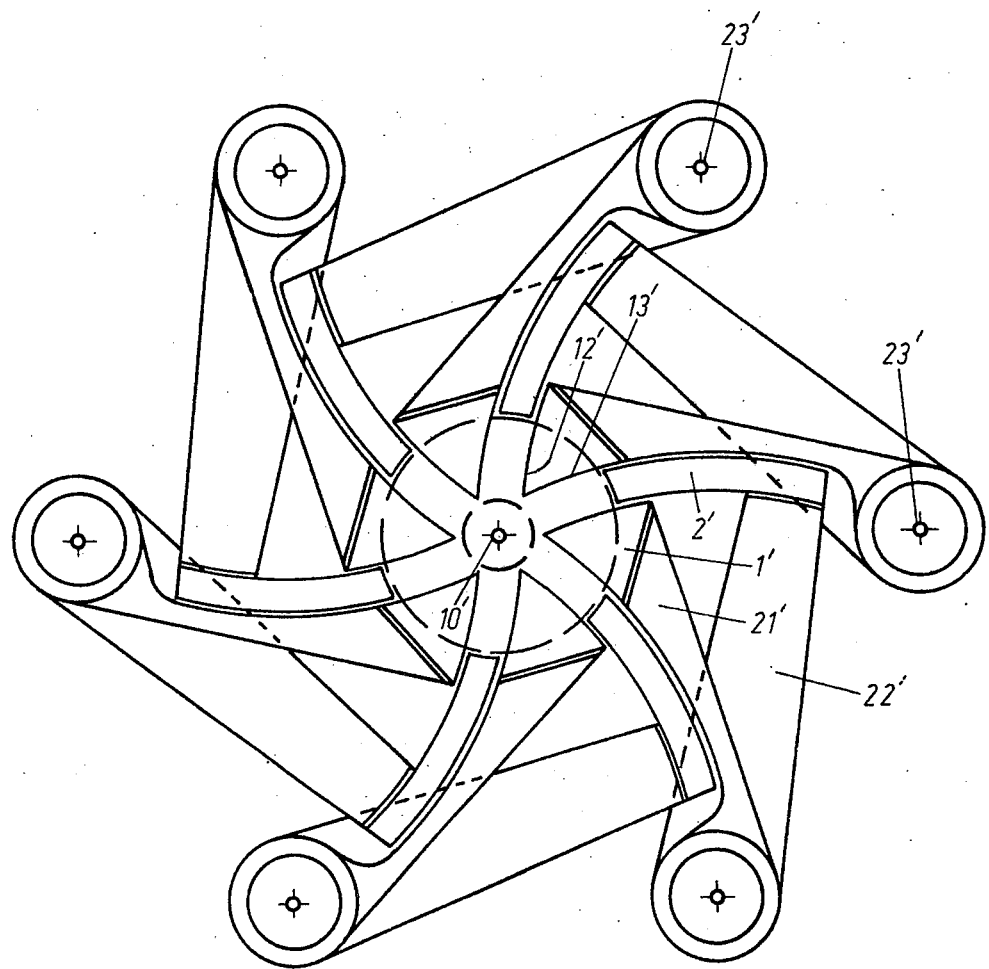

FIGS. 6 and 7 respectively show the loading of a blank and the ejection of a compressed tampon using the machine of FIG. 1; and FIG. 8 is a schematic plan view of a modified embodiment of the invention.

The machine shown in FIG. 1 has a first set of pressing dies 1 containing $n$ number of dies therein, $n$ being four ($n = 4$) as illustrated, which are arranged around the four sides of a central axis 10 and movable theretowards, each die 1 having two adjoining pressing surfaces 12 and 13, which intersect at an angle of about 90° ($360°/n = 360°/4$) to define a pressing edge 11 extending parallel to axis 10. A second set of pressing dies 2 also $n$ in number, $n$ being 4, are disposed each between one adjacent pair of the dies 1 arranged around axis 10, for movement towards axis 10 in the clearance space between the pairs of first dies 1, each die 2 having at its inner end a concave pressing surface 14 in the form of a groove or shallow concavity extending parallel to axis 10. At the ends of each pressing surface 12 and 13 on the dies 1 are free edges 25 and 24, respectively. Each die in the first set 1 is carried at the inner end of double-armed bell crank 21 mounted for pivotal movement about a pivot axis 23, the axes 23 being arranged generally in a square around center axis 10. The arms of crank 21 are linked together on three sides by links 19 and on the fourth side by a triangular link 17 which is connected at its apex to an operating rod 15 so that as rod 15 is reciprocated, the dies of set 1 move together equally in concert toward or away from axis 10. Similarly each of the dies of set 2 is carried at the inner end of a double-armed bell-crank 22 which is also pivoted about the axis 23 of the crank 21 for an adjacent die of set 1 and the arms of crank 22 are linked on three sides by links 20 and on the front side by triangular link 18 connected to operating rod 16. Thus, as rod 16 reciprocates, the dies of set 2 swing towards or away from axis 10 equally in concert as a unit.

Pivots 23 are all located the same distance away from axis 10, which distance is indicated at R (see FIG. 2), while the distance between adjacent pivots 23 is $2 R \cdot \sin \pi/4 = 2R \cdot \frac{1}{2}\sqrt{2} = \sqrt{2} \cdot R$.

Figure 4:
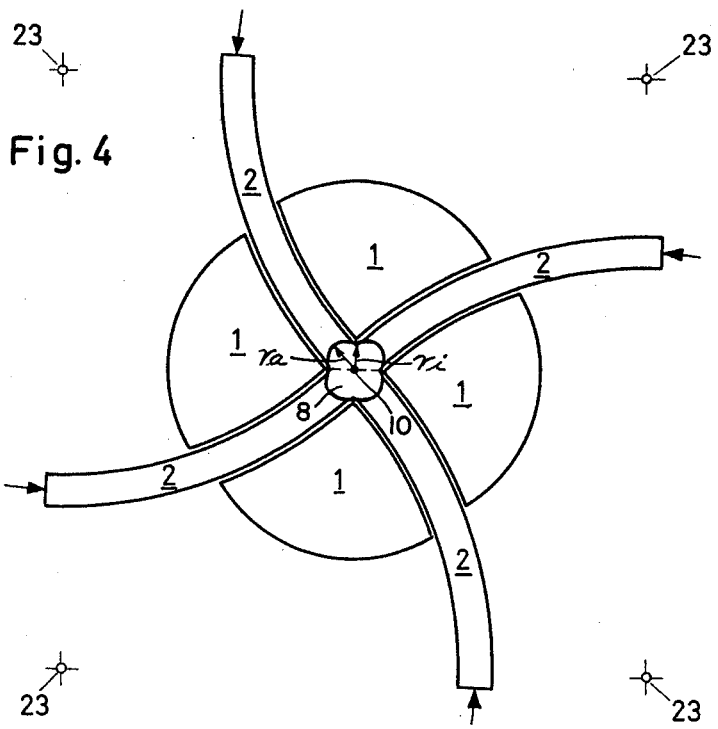
Figure 5:
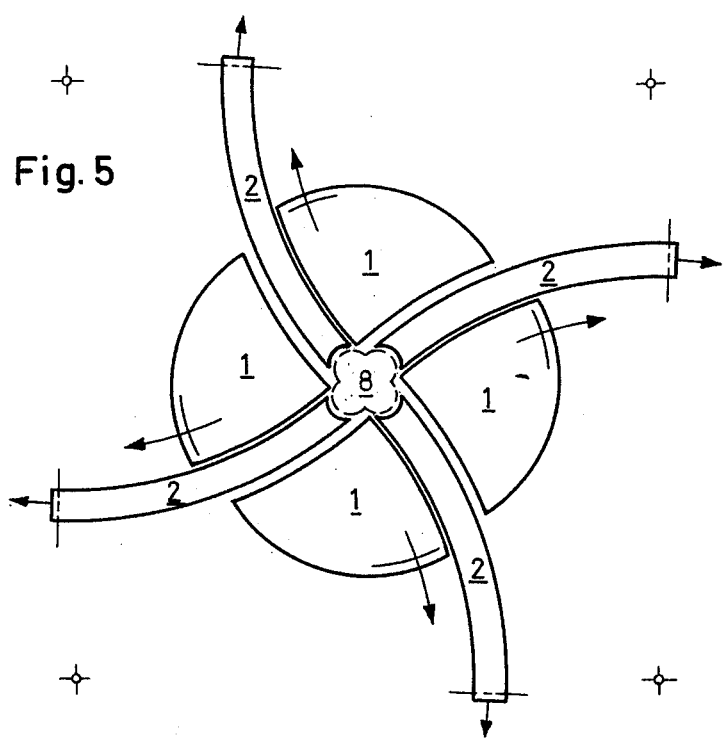

During manufacture of the tampon, a substantially cylindrical tampon blank 6 is introduced between the dies of sets 1 and 2 while the latter are displaced outwardly of axis 10 and the distance R must be greater than half the diameter D of the blank 6 (see FIG. 2) in order to create space for the blank to be received. Furthermore, R must be at least $$\frac{D}{4} \{ (k + \sin \frac{\pi}{4}) \} c^2/k$$

wherein $$k = \frac{1 - c \sin \frac{\pi}{4}}{1 - \sin \frac{\pi}{4}}$$

and $c = 2 r_i/D$, $r_i$ being the smallest distance of the external surface of a fully compressed tampon designated 8 in FIGS. 4 and 5 from the centre of tampon 8, i.e. for example the distance between the axis 10 and the bottom of one of the four peripheral grooves seen on the tampon 8 in FIG. 4 (corresponding to edge 11 of dies 1). The last-mentioned requirement arises from the fact that free edges 24 of surfaces 13 of the first dies 1 need not touch the blank 6 during pivot of the first dies 1. For $n = 4$, R is at least $0.854 D - 1.207 r_i + 0.5 r_i^2/D$. Both requirements, i.e. the last-mentioned requirement and the fact that R must be greater than $d/2$, are fulfilled in the machine illustrated in FIG. 1, where $R \approx 1.6 D$.

The two surfaces 12 and 13 of the first dies 1 are both arcuate and generally converge at an included angle equal to about $360°/n$. As mentioned, each die 1 is associated with a second die 2 pivotable alone with the associated die 1 about a common pivot axis 23, and the surface 12 of die 1 forms a convexly-curved sector of a cylinder with a surface having a radius of curvature of at least approximately $p \cdot R$, wherein $p = \sqrt{1 - r_i^2/2R^2} - r_i/\sqrt{2} R$ and $r_i$ is as hereinbefore defined. The axis of this sector is coaxial with the axis 23 for the corresponding pressing surface 12. The sector angle of this sector, i.e. the effective length of surface 12 between edges 11 and 25 must, when $n = 4$, be at least $$\alpha_{min} = \arccos \cdot \{ \frac{1}{2} (p + \frac{1}{p}) - D^2/8 \, p \, R^2 \} - \arcsin \frac{r_i}{\sqrt{2R}}.$$

This requirement arises from the fact that the free edges 25 of the convex surfaces 12 of the first dies 1 should be spaced a distance of at least D/2 from axis 10 when the dies 1 are in fully pivoted position (see FIG. 3). This is because the pivotal movement of dies 1 does not substantially lessen the effective diameter of the portions of the blank remaining in the gaps between the cooperating surfaces 12 and 13 of adjacent dies 1. As an approximation, this last requirement can be expressed by stating that the minimum sector angle $\alpha_{min}$ for $n = 4$ is 28.7°. $D/Rp - 40.5° \, r_i/R$. This requirement is fulfilled in the illustrated machine when the sector angle of the sector of the cylinder formed by surface 12 is 17.2° and this is only approximately 2° more than the minimum sector angle $\alpha_{min}$ of 15.2° required in the present case.

Each pressing surface 13 of the first die is in the form of a concave cylindrical sector with a radius of curvature of at least approximately $(p + 2 q) R$, in which $p = \sqrt{1 - r_i^2/2R^2} - r_i/\sqrt{2} \cdot R$, $q = r_i/\sqrt{2} \cdot R$, and $r_i$ is as hereinbefore defined. The free edges 24 of the concave surfaces 13 of the first dies 1 should be at a distance of at least D/2 from axis 10 after pivoting of the first dies 1 for the same reason explained above for surfaces 12. This requirement, however, leads to a rather smaller sector angle, i.e. less than $\alpha_{min}$, for the concave cylindrical sector formed by surface 13, as the radius of curvature of its surface is greater than the radius of curvature of the convex surface 12 by $\sqrt{2} \cdot r_i$.

If only this minimum requirement were filled for the sector angle of the concave sector forming surfaces 13, after pivoting of the first dies 1 the inner grooved edges of the dies 2 would be further away from axis 10 than edge 24 so that a gap or space would remain between the free edge 24 of surface 13 and the adjacent or facing side of the adjoining die 2. This is undesirable because with compression of blank 6 during pivoting of dies 1, tampon material could protrude into this space, and this would lead to obstruction of free pivotal movement of dies 2. Naturally, dies 2 would cut off or pinch off this tampon material as they swing inwardly, but this cut off or pinched off material would accumulate in the machine and after a while it would cause breakdowns. Cutting off or pinching off of protruding tampon material by dies 2 would also cause asymmetrical loadings on dies 2, and thereby introduce considerable vibration when the machine was operating. This again would lead to considerable increase in wear. A further reason why gaps are undesirable is that it would then be necessary to provide separate abutments for the first dies 1 for limiting the inward pivotal movement. If the pressing surfaces 12 are long enough to simply abut against the second dies 2 at the end of their movement, separate abutments can be dispensed with. For the reasons indicated above, the sector angle of the sector forming surface 13 is also preferably at least $\alpha_{min}$. The sector angles $\alpha$ and $\beta$ of the two sectors formed by the two surfaces 12 and 13 of each first die 1 are preferably greater than $\alpha_{min}$. This can also be fulfilled by the machine illustrated in FIG. 1, where $\alpha_{min} = 15.2°$ and $\alpha = 17.2°$, and $\beta = 16.5°$. For reasons of symmetry, it is of advantage if the two sector angles $\alpha$ and $\beta$ are generally equal in magnitude, in particular if the seconds dies 2 are also to operate as abutments for limiting the pivotal inward movements of the first dies 1.

Each die 2 is a hollow cylindrical sector with an annular thickness of at least approximately $\sqrt{2} \cdot r_i$, a concave surface radii of curvature close to $p \cdot R$ and a convex surface radii of curvature of at least approximately $(p - 2 q) R$, where $p = \sqrt{1 - r_i^2/2 R^2} - r_i/\sqrt{2} R$ and $q = r_i/\sqrt{2} \cdot R$. The cylinder axis of this annular cylindrical sector coincides with the pivot axis 23 for the particular die 2. The inner edge face of this sector towards axis 10 is concave and forms the groove-like pressing surface 14 on each die 2. The depth of the concavity of surface 14 should be at least approximately $r_a - r_i/\sqrt{2}$, where $r_a$ denotes the maximum dimension of the external surface of a fully compressed tampon 8 from the centre of the tampon 8, (i.e. half the greatest diameter of tampon 8 in FIG. 4), and $r_i$ is as hereinbefore defined. Furthermore, surface 14 is curved symetrically relative to its center and is advantageously cylindrical with a radius of curvature $r_i$. In this case, $r_a$ will be equal to $r_i$, i.e. the blank 6 is compressed to a dense cylindrical form with diameter equal to $2 \cdot r_i$. If, on the other hand, definite grooves are desired in the peripheral surface of the tampon between its four external surface sectors defined by grooves 14, $r_a$ should be greater than $r_i$, and the pressing surface 14 is then advantageously in the form of a sector symmetrical with the great elliptic half-axis of the surface of an elliptical cylinder, or of parabolic cross-section.

The drive rods 15 and 16 are movable alternately in their lengthwise direction, for example pneumatically by compressed air cylinders, magnetically by electromagnets, or by eccentric discs and an electric motor, preferably a stepping motor, in rhythm with the required opening and closing movements of the die sets 1 and 2. Linear movements of drive rods 15 and 16, with the aid of coupling links 17, 19 and 18, 20, respectively plus the double arms at the rear end of each crank 21 or 22, are converted into corresponding pivotal movement for these arms and thereby of the respective dies 1 and 2.

FIGS. 2 to 5 show various stages of movement of the dies 1 and 2.

Initially, dies in sets 1 and 2 are in their open or separated position shown in FIG. 2. A tampon blank 6 is loaded, as FIG. 6 shows, by a two-part punch 3, 4 into the space between the open die sets 1 and 2. The punch 3, 4 is withdrawn after loading, so that the end surface of the cylindrical punch member 4 is in substantially the same vertical plane as the upper walls of dies 1 and 2.

The first set of dies 1 is then pivoted into the compression position shown in FIG. 3, whereby the blank 6 is compressed to an intermediate conformation 7 which is substantially cruciform, i.e. x-shaped, in cross-section. The paths followed by the dies 1 in this operation are shown by chain lines in FIG. 2 and by arrows in FIG. 3. The pressing forces caused by this movement do not pass through the central region of the blank 6, and in practice only the "arms" of the cruciform intermediate conformation 7 generated from the blank 6 are compressed in a direction generally transverse to their length. After pivoting the first dies 1, tampon material in the central area of the cross-shaped conformation 7 has not been compressed, while tampon material in the airm of the cross-shaped conformation 7 has been compressed substantially, i.e. by a factor of 2.25.

After pivoting of the first dies 1 is complete, the second set of dies 2 is pivoted into their compression position shown in FIG. 4. The cross-shaped conformation 7 is then compressed to the final tampon 8, which can be seen in FIG. 4. The movement performed by the dies 2 will clearly be seen on comparing FIGS. 3 and 4. It will also been from FIG. 3 that the end pressing surfaces of the dies 2 are not directed exactly towards the center of intermediate conformation 7 at the start of pivoting of the dies 2, so that pressing forces acting directly against the center of the pressed blank only arise during a latter portion of movement of dies 2. In the present case, this latter portion is a relatively large proportion of the overall movement of the second dies, because the ratio R/D is selected to be 1.6, which is relatively high. By reducing the ratio R/D, e.g. to 0.7 to 0.8, this latter portion of movement is substantially reduced and amounts, for example, to only 15 to 30% of the overall extent of movement. On pivoting the second dies 2, tampon material is compressed principally in edge areas to a smaller or greater extent depending on the ratio of R/D, while compression at the center of the manufactured tampon 8 is smaller than with the known machines referred to hereinbefore.

When the second dies 2 are completely pivoted, the pressing process is complete, and the dies 1 and 2 can be returned to their respective starting positions shown in FIG. 1. Early in this pivoting-away process, and therefore while the dies are substantially in the position shown in FIG. 5, the completed tampon 8 is ejected by means of the cylindrical punch member 4 which can have a nose 9, as shown in FIG. 7. After the dies 1 and 2 have returned to the respective positions shown in FIG. 1, a new pressing process can then begin.

Using the machine of the present invention, it is possible to achieve thickening or compression of tampon material in edge areas of the tampon which are evenly distributed around the periphery of the tampon. As a result, the tampons have a substantially improved resistance to buckling. The compressive forces of the first pressing dies 1 are not applied directly against the central areas of the tampon being manufactured, rather, they follow lines offset from this central area. Furthermore, the compressive forces created subsequently by the second dies are initially inclined away from this central area and are not directed towards the exact center of the tampon until near the end of that movement. Consequently, only minimum compression of the tampon material takes place in the central area of the tampon. When using the known machine referred to above, the compressive forces of the first pressing dies act directly against the central areas of the tampon being manufactured and which are greater by a factor of $\cos \pi/n$ times the compressing forces in this invention. Furthermore, the compressive forces caused by the second dies are directed directly against the center of the tampon, which naturally has as a consequence a considerably higher compression of the tampon material at the center and a correspondingly smaller compression in the external edge areas thereof than results with the machine of the invention. As a result, the buckling resistance of tampons manufactured by the present machine is considerably greater than that of tampons manufactured using the known machine referred to hereinbefore.

Preferably $n$ is at most equal to 6, and the distance R of the pivot axes from the central axis of the machine is greater than $$\frac{D}{4\left(1 - \sin \frac{\pi}{n}\right)}.$$

There is shown in FIG. 8 a modification of the invention employing six pressing dies in each of the sets 1 and 2, prime numerical designations being used for elements in common with the main embodiments of the other figures.

I claim:

1. A machine for manufacturing tampons, which comprises a plurality of pressing dies arranged as a first set around a common central axis for movement along similar arcuate paths between a separated position spaced from said common axis for receiving a tampon blank and a compression position adjacent said axis for compressing the blank into a shaped tampon, each such first die having generally converging arcuately curved concave and convex surfaces which include therebetween an angle equal to about 360° divided by the number of dies in said first set with these surface curvatures when said first set is in said compression position generally mating respectively with the respectively adjacent convex and concave surfaces of other dies of said set situated on either side to define a narrow arcuately curved gap or slot between the mutually mating surfaces of each adjacent pair of first dies; a cooperating plurality of pressing dies arranged in a second set around said axis for movement within the arcuately curved gaps or slots between adjacent pairs of first dies from a separated to a compression position after the first dies are in their compression position, each die in said second set having opposed concave and convex surfaces mating with the curvatures of the mutually facing surfaces of each pair of first dies which define such gap and terminating at its inner end in a compressing face; separate operating means for moving the dies in each set substantially simultaneously between said positions and independently of the other set, and means for loading a tampon blank into the space between the dies while in a separated position and for ejecting the compressed tampon.

2. The apparatus of claim 1 wherein said inner compression face on each second die is concavely curved.

3. The apparatus of claim 1 wherein the convex and concave surfaces of each said first die intersect along a common edge on the side of the die generally facing common central axis.

4. The apparatus of claim 1 wherein said operating means comprises first drive means for moving the first set of pressing dies between said positions; second drive means for moving the second set of pressing dies between said positions; first coupling means for coupling the dies in said first set together so that corresponding points on the first dies are spaced at equal distances from said central axis during their movement; and second coupling means for coupling the dies in said second set together so that corresponding points on the second dies are spaced equal distances from said central axis during their movement.

5. The apparatus of claim 1 wherein the dies of the respective sets are mounted for pivotal movement about axes arranged around and in spaced relation to said central axis.

6. The apparatus of claim 5 wherein each of the second dies shares a common pivot axis with a different one of the first dies.

7. The apparatus of claim 6 wherein each pivot axis common to a first and an adjacent second pressing die is spaced a distance R from said central axis and a distance $2 R \sin \pi/n$ from adjacent pivot axes, R being greater than $D/2$ and equal to at least $D/4 \{k + (1 - \sin \pi/n)c^2/k\}$, wherein D is the diameter of the blank, $c = 2r_i/D$ where $r_i$ is the minimum radius of the compressed tampon, n is the number of dies in each set and $$k = \frac{1 - c \sin \frac{\pi}{n}}{1 - \sin \frac{\pi}{n}}.$$

8. The apparatus of claim 7 wherein said convex surface has a radius of curvature relative to the pivot axis of said first die of at least approximately $p \cdot R$ wherein $p = \sqrt{1 - q^2} \tan \pi/n$, q being equal to $a \cos \pi/n$ with $a = r_i/R$ and $r_i$ and R are as defined in claim 17, and extends over a sector included within a sector angle of at least $\alpha_{min} = \arc \cos$ $$\{ \frac{1}{2}(p + \frac{1}{p}) - \frac{d}{p} \} - \arc \sin q,$$

where $d = D^2/8 R^2$ and said concave surface has a radius of curvature relative to the pivot axis of an adjacent first die of at least approximately $\{p + 2 q \tan \pi/n\}$ R.

9. The apparatus of claim 8 wherein each second pressing die is in the form of a sector of an annulus having a wall thickness of at least approximately $2 q \tan \pi/n \cdot R$, a concave surface with a radius of curvature relative to the pivot axis of said second die of at least approximately $p \cdot R$, and a convex surface having a radius of curvature relative to the pivot axis of said second die of at least approximately $\{p + 2 q \tan \pi/n\}$ R.

10. The apparatus of claim 9 wherein the inward compression surface of said second die has a concave surface opening towards said central axis which has a concave depth of at least approximately $(b - q)$ R, wherein $b = r_a/R$, and q and R are as defined above.

11. A machine according to claim 1, wherein the sector angle of the opposed concave and convex surfaces defining each second die is greater than the sector angles of the mutually adjacent concave and convex surfaces defining the slot wherein said second die moves.

* * * * *

UNITED STATES PATENT OFFICE
CERTIFICATE OF CORRECTION

Patent No. 4,109,354    Dated August 29, 1978

Inventor(s) Marcel Ronc

It is certified that error appears in the above-identified patent and that said Letters Patent are hereby corrected as shown below:

Claim 8, line 4, "$p = \sqrt{1 - q^2} \tan \pi/n$" should read -- $p = \sqrt{1 - q^2} - q \tan \pi/n$ --.

Signed and Sealed this

Thirteenth Day of February 1979

[SEAL]

Attest:

RUTH C. MASON
Attesting Officer

DONALD W. BANNER
Commissioner of Patents and Trademarks